(12) United States Patent
Day et al.

(10) Patent No.: US 9,664,565 B2
(45) Date of Patent: *May 30, 2017

(54) LIBS ANALYZER SAMPLE PRESENCE DETECTION SYSTEM AND METHOD

(71) Applicant: SciAps, Inc., Woburn, MA (US)

(72) Inventors: David R. Day, Boxford, MA (US); Donald W. Sackett, Bedford, MA (US)

(73) Assignee: SciAps, Inc., Woburn, MA (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/632,419

(22) Filed: Feb. 26, 2015

(65) Prior Publication Data

US 2016/0252397 A1 Sep. 1, 2016

(51) Int. Cl.
| | |
|---|---|
| *G01J 3/30* | (2006.01) |
| *G01J 3/443* | (2006.01) |
| *G01J 3/10* | (2006.01) |
| *G01J 3/02* | (2006.01) |

(52) U.S. Cl.
CPC ............. *G01J 3/443* (2013.01); *G01J 3/027* (2013.01); *G01J 3/10* (2013.01)

(58) Field of Classification Search
CPC ...... G01J 3/02; G01J 3/443; G01J 3/10; G01J 3/0248; A61F 9/008
See application file for complete search history.

(56) References Cited

U.S. PATENT DOCUMENTS

| | | | |
|---|---|---|---|
| 3,760,144 A | 9/1973 | Herzberger | |
| 4,358,659 A | 11/1982 | Spohnheimer | |
| 5,473,162 A | 12/1995 | Busch et al. | |
| 5,520,679 A | 5/1996 | Lin | |
| 6,077,386 A | 6/2000 | Smith, Jr. et al. | |
| 6,355,908 B1 | 3/2002 | Tatah et al. | |
| 6,801,595 B2 | 10/2004 | Grodzins et al. | |
| 7,233,643 B2 | 6/2007 | Sipilä et al. | |
| 7,394,537 B1 | 7/2008 | Lindfors et al. | |
| 7,676,061 B2 | 3/2010 | Harrison et al. | |

(Continued)

FOREIGN PATENT DOCUMENTS

| | | |
|---|---|---|
| WO | WO 2012/040769 A1 | 4/2012 |
| WO | WO 2012/135961 A1 | 10/2012 |

(Continued)

OTHER PUBLICATIONS

Written Opinion of the International Searching Authority for PCT Application No. PCT/US2014/11961 mailed May 8, 2014 (six (6) pages).

(Continued)

*Primary Examiner* — Tarifur Chowdhury
*Assistant Examiner* — Jamil Ahmed
(74) *Attorney, Agent, or Firm* — Iandiorio Teska & Coleman, Inc.

(57) ABSTRACT

A LIBS analyzer, preferably handheld, includes a laser configured to produce a plasma on a sample and a spectrometer responsive to radiation emitted from the plasma and configured to produce a spectrum. A controller subsystem is configured to control energizing the laser and to analyze the resulting spectrum from each laser pulse to determine if the laser is aimed at a sample. If the analyzed spectrum reveals the laser is not aimed at the sample, the controller subsystem halts the laser puke sequence.

19 Claims, 5 Drawing Sheets

(56) References Cited

U.S. PATENT DOCUMENTS

| | | |
|---|---|---|
| 7,821,634 B2 | 10/2010 | Dillon et al. |
| 8,184,287 B2 | 5/2012 | Hamilton et al. |
| 8,436,991 B2 | 5/2013 | Senac |
| 8,576,382 B2 | 11/2013 | LaValley et al. |
| 2001/0015801 A1 | 8/2001 | Hirose et al. |
| 2002/0009814 A1 | 1/2002 | Usui et al. |
| 2003/0010907 A1 | 1/2003 | Hayek et al. |
| 2003/0174325 A1 | 9/2003 | Zhang et al. |
| 2003/0234928 A1 | 12/2003 | Lucas et al. |
| 2004/0183010 A1 | 9/2004 | Reilly et al. |
| 2005/0056628 A1 | 3/2005 | Hu |
| 2005/0068524 A1 | 3/2005 | Wu et al. |
| 2005/0236563 A1 | 10/2005 | Busch et al. |
| 2005/0248758 A1 | 11/2005 | Carron et al. |
| 2006/0100676 A1 | 5/2006 | Walmsley |
| 2006/0262302 A1 | 11/2006 | Eklin |
| 2007/0187632 A1 | 8/2007 | Igarashi |
| 2007/0195311 A1 | 8/2007 | Morgan |
| 2007/0202613 A1 | 8/2007 | Usul |
| 2007/0265783 A1 | 11/2007 | Mound |
| 2008/0151241 A1 | 6/2008 | Lindfors et al. |
| 2008/0165344 A1 | 7/2008 | Treado et al. |
| 2008/0205755 A1 | 8/2008 | Jackson |
| 2008/0259330 A1 | 10/2008 | Dillon et al. |
| 2009/0007933 A1 | 1/2009 | Thomas et al. |
| 2009/0025761 A1 | 1/2009 | Matsumoto |
| 2009/0057422 A1 | 3/2009 | Dugas et al. |
| 2009/0103082 A1 | 4/2009 | Black et al. |
| 2010/0197116 A1 | 8/2010 | Shah et al. |
| 2011/0315661 A1 | 12/2011 | Morisawa |
| 2012/0029836 A1 | 2/2012 | Hermann |
| 2012/0044488 A1 | 2/2012 | Senac |
| 2012/0085366 A1 | 4/2012 | Hirota |
| 2012/0162642 A1 | 6/2012 | Watson et al. |
| 2012/0206722 A1 | 8/2012 | Grigoropoulos et al. |
| 2012/0236303 A1 | 9/2012 | Marple et al. |
| 2012/0268743 A1 | 10/2012 | Wang et al. |
| 2012/0310141 A1* | 12/2012 | Kornfield ............... A61F 9/008 604/20 |
| 2012/0314214 A1 | 12/2012 | Alexander et al. |
| 2013/0016349 A1 | 1/2013 | Effenberger, Jr. et al. |
| 2013/0342902 A1 | 12/2013 | Krueger |
| 2014/0022531 A1 | 1/2014 | Sackett |
| 2014/0022532 A1 | 1/2014 | Sackett |
| 2014/0125965 A1 | 5/2014 | Nagli |
| 2014/0202490 A1 | 7/2014 | Day |
| 2014/0204375 A1 | 7/2014 | Day |
| 2014/0204376 A1 | 7/2014 | Day |
| 2014/0204377 A1 | 7/2014 | Day et al. |
| 2014/0204378 A1 | 7/2014 | Day |
| 2016/0178434 A1* | 6/2016 | Buckley ............... G01J 3/0248 356/72 |

FOREIGN PATENT DOCUMENTS

| | | |
|---|---|---|
| WO | WO 2013/083950 A1 | 6/2013 |
| WO | WO 2015/057784 | 4/2015 |

OTHER PUBLICATIONS

Written Opinion of the International Searching Authority for PCT Application No. PCT/US2014/11863 mailed May 13, 2014 (nine (9) pages).

Written Opinion of the International Searching Authority for PCT Application No. PCT/US2014/16188 mailed Feb. 2, 2015 (eight (8) pages).

Written Opinion of the International Searching Authority for PCT Application No. PCT/US2014/12060 mailed Jan. 27, 2015 (five (5) pages).

Oxford Instruments, Laser Induced Breakdown Spectroscopy (LIBS), http://www.oxford-instruments.com/products/spectrometers/laser-induced-bre . . . , (two (2) pages), 2014.

Applied Spectra, Inc., Model RT100-EC, http://www.appliedspectra.com/products/rt100-ec.html, (four (4) pages), 2004-2013.

RMG Technology Introduces Hand-Held Laser Analyzer, Recycling Today, May 29, 2013 http://www.recyclingtoday.com/Article.aspx?article_id=141665, (two (2) pages), May 29, 2013.

Ocean Optics, Laser-Induced Breakdown Spectroscopy, The LIBS2500plus LIBS Systems, http://www.oceanoptics.com/products/libs.asp, (four (4) pages), 1989-2012.

Applied Photonics, LIBSCAN 25, brochure, (two (2) pages), 1998-2010.

Comite Europeen de Normalisation Electrotechnique (CENELEC), "Safety of Laser Products—Part 1: Equipment classification requirements", British Standard BSi, (IEC 60825-1:2007), Oct. 2007, 3 pages.

CFR—Code of Federal Regulations Title 21, "Title 21—Food and Drugs, Chapter I—Food and Drug Administration, Department of Health and Human Services, Subchapter J—Radiological Health", Revised as of Apr. 1, 2014, 16 pages.

Laser Institute of America, "American National Standard for Safe Use of Lasers", ANSI Z136.1-2007, © 2007, 21 pages.

U.S. Department of Labor, "OSHA Technical Manual (OTM)—Section III: Chapter 6", https://www.osha.gov/dts/osta/otm/otm_iii_6.html, effective date Jan. 20, 1999, 29 pages.

* cited by examiner

LIBS ANALYZER SAMPLE PRESENCE DETECTION SYSTEM AND METHOD

RELATED APPLICATIONS

This application is related to U.S. patent application Ser. Nos. 13/746,110 filed Jan. 21, 2013; Ser. No. 13/746,095 filed Jan. 21, 2013; Ser. No. 13/746,108 filed Jan. 21, 2013; Ser. No. 13/746,102 filed Jan. 21, 2013; Ser. No. 14/179,670, filed Feb. 13, 2014 and Ser. No. 14/608,359 filed Jan. 29, 2015, all are incorporated herein by this reference.

FIELD OF THE INVENTION

The subject invention relates to laser induced breakdown spectroscopy (LIES).

BACKGROUND OF THE INVENTION

Lasers have been classified according to the potential for causing biological damage. The Laser Institute of America Standard ANSIZ136.1 is used to classify lasers. Government organizations also have standards for the use of lasers. See, for example, 29 C.F.R. 1926.102(b)(2) and 21 C.F.R. 1040. In general, Class I (eye safe) lasers do not emit radiation at known hazard levels. For higher class lasers, eye protection, training, safety protocols, and the like may be required. This is not generally true for Class I lasers.

Those skilled in the art have devised various safety measures for lasers. For example, in U.S. Pat. No. 8,576,382, incorporated herein by this reference, disclosed is the use of a non-eye safe laser (in a LIBS system, for example). The operational range to the intended target is known and if a range unit determines the range to the target while the system is in use is greater than the operational range of the system, the non-eye safe laser is disabled. See also U.S. Pat. No. 7,676,061 incorporated herein by this reference.

In some applications, an eye safe laser for a handheld LIBS analyzer is desired. See U.S. patent application Ser. Nos. 13/746,110 and 14/179,670 by the assignee hereof incorporated herein by this reference. One reason for incorporating an eye safe laser is to eliminate the regulatory requirements placed on higher class lasers. Still, a higher power (e.g., 6-8 mJ) laser may be needed to detect certain elements in certain samples or targets. A higher power laser may also provide lower detection limits.

SUMMARY OF THE INVENTION

Herein, a higher power laser can be used and may still be classified as a Class I laser since the LIES analyzer includes a protection scheme to cease operation of a higher power laser if it is not aimed at a sample to be analyzed. The result is a safe LIES system which may not require protective eyewear or training.

Featured is a LIBS analyzer comprising a laser configured to produce a plasma on a sample and a spectrometer responsive to radiation emitted from the plasma and configured to produce a spectrum. A controller subsystem is configured to control energizing of the laser and includes computer instructions which initiate a laser pulse sequence in response to a fire command and analyze the resulting spectrum from each laser pulse to determine if the laser is aimed at a sample. If the analyzed spectrum reveals the laser is aimed at the sample, the controller continues pulsing the laser to test the sample for a test duration. If after any pulse, the analyzed spectrum reveals the laser is not aimed at the sample, the controller halts the laser pulse sequence.

In one example, testing the sample includes pulsing the laser at 10 Hz or greater and analyzing the spectrum between pulses. The LIBS analyzer controller subsystem may be further configured to generate a message if the analyzed spectrum reveals the laser is not aimed at the sample.

In one aspect, the laser preferably has a power, a wavelength range, and an emission duration which meets the class I single pulse ANSI standard. In one example, the power is 8 mJ or less, the wavelength range is 1500-1800 nm, and the emission duration is $10^{-7}$-$10^{-9}$ seconds. Analyzing the resulting spectrum for each laser pulse by the controller subsystem may include measuring the maximum signal in a predetermined wavelength range of the spectrum. The LIES analyzer controller subsystem computer instructions may be configured to automatically halt the laser pulse sequence if the maximum signal amplitude in a predetermined wavelength range of the spectrum is less than a predetermined amplitude. In one example, the predetermined amplitude is 200 and the predetermined wavelength range is 200-400 nm. The LIBS analyzer controller subsystem computer instructions preferably automatically continue the test if the maximum signal amplitude in the predetermined wavelength range is greater than the predetermined amplitude.

Also featured is a LIES analysis method comprising initiating a laser pulse sequence in response to a firing command, receiving radiation and providing a spectrum for each laser pulse, analyzing the spectrum to determine if the laser is aimed at a sample and producing a plasma on the sample, continue pulsing the laser to test the sample if the analysis reveals the laser is aimed at the sample, and stopping the test if the analysis reveals the laser is not aimed at the sample.

Also featured is a LIBS analyzer comprising a laser having a power, a wavelength range, and an emission duration which meets a class I single pulse laser standard. A spectrometer is responsive to radiation emitted by a plasma created by the laser beam and configured to produce a spectrum. A controller subsystem is configured to initiate a laser pulse sequence, analyze the resulting spectrum for each laser pulse, halt the laser pulse sequence if a maximum signal amplitude in a predetermined wavelength range of the spectrum is less than a predetermined amplitude, and continue pulsing the laser if the maximum signal amplitude in the predetermined wavelength range of the spectrum is greater than the predetermined amplitude.

Also featured is a LIBS analyzer comprising a laser having a power, a wavelength of 1064 nm, and an emission duration which meets a class 3b safety standard. A spectrometer is responsive to radiation emitted by a plasma created by the laser beam and configured to produce a spectrum. A controller subsystem is configured to initiate a laser pulse sequence, analyze the resulting spectrum for each laser pulse, halt the laser pulse sequence if a maximum signal amplitude in a predetermined wavelength range of the spectrum is less than a predetermined amplitude, and continue pulsing the laser if the maximum signal amplitude in the predetermined wavelength range of the spectrum is greater than the predetermined amplitude. In this particular example, even though the laser class remains at a 3b rating, for misuse of the device at most a single laser pulse can escape the device. Without the pulse spectral monitoring, an operator could fire a large number of laser pulses that miss the sample potentially striking an operator or bystander's eyes.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
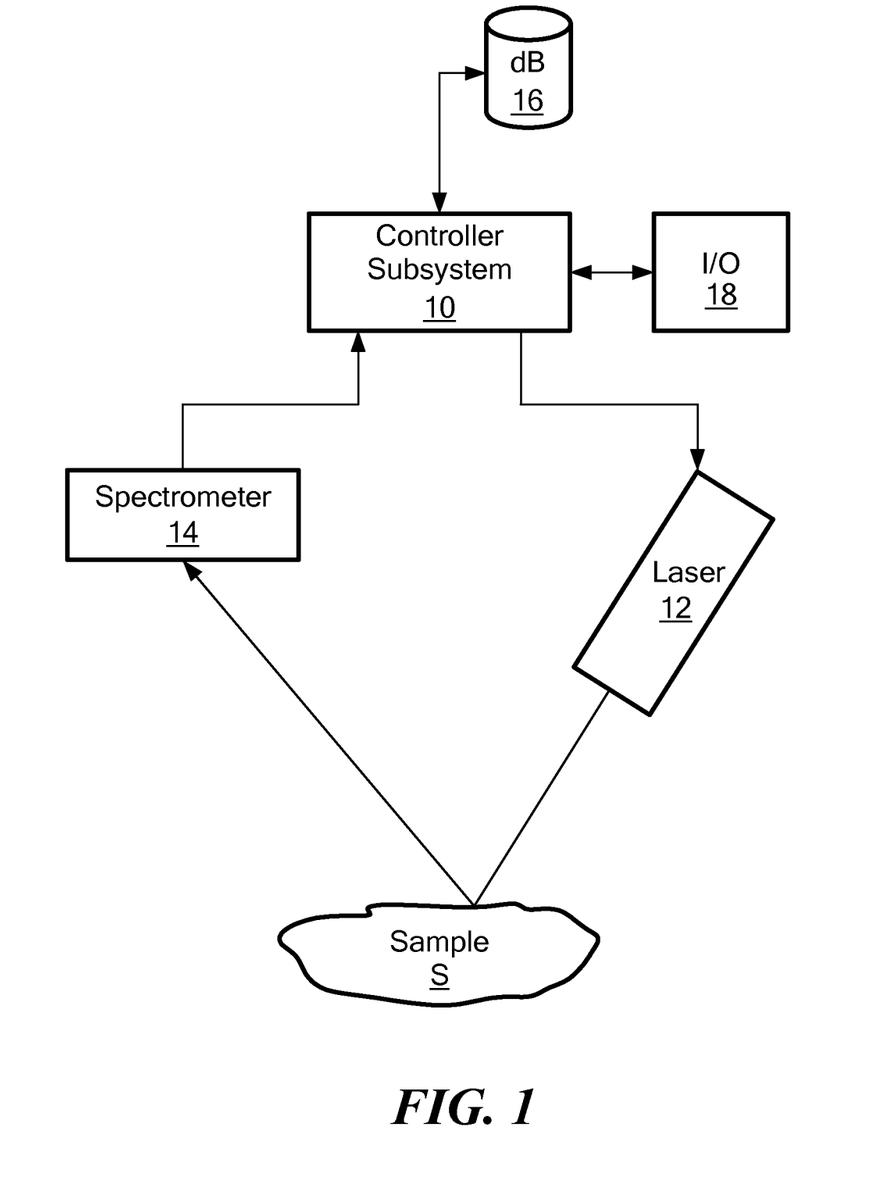
FIG. 1 is a simplified schematic block diagram showing the primary components associated with a LIBS analyzer in accordance with aspects of the invention.

FIG. 1 shows a LIBS system, preferably a handheld analyzer as disclosed in co-pending application U.S. Ser. Nos. 13/746,110 and 14/179,670 incorporated herein by this reference. Controller subsystem 10 controls the energizing of a laser 12 (e.g., 3-8 mJ) to produce a laser beam striking sample S producing a plasma thereon. Typically, the nose section of the handheld LIBS analyzer is designed to be placed directly on sample S. Spectrometer 14 is located to receive radiation from the resulting plasma and produces a spectrum of wavelength intensities in order to determine the elements and their concentration present in sample S based for example, on a spectral library populating database 16 stored in a memory device such as a PROM, EEPROM, flash memory or the like.

Spectrometer 14 may include its own processing capabilities or controller subsystem 10 may include one or more processors programmed to analyze spectral data (from a CCD, for example) produced by one or more spectrometers 14. Different spectrometers may be tailored for different wavelength ranges.

Controller subsystem 10 may include one or more processors as noted above, one or more microcontrollers, applications specific integrated circuits, field programmable gate arrays, or the like carrying out the functions described herein (typically by loading and running computer instructions stored in memory). Input/output section 18 can be used to trigger a firing command (via the push of a trigger or button on the handheld LIBS analyzer, for example). Input/output section 18 typically also includes a display such as a touch screen display for displaying messages, spectral information, test results, and the like.

Figure 2:
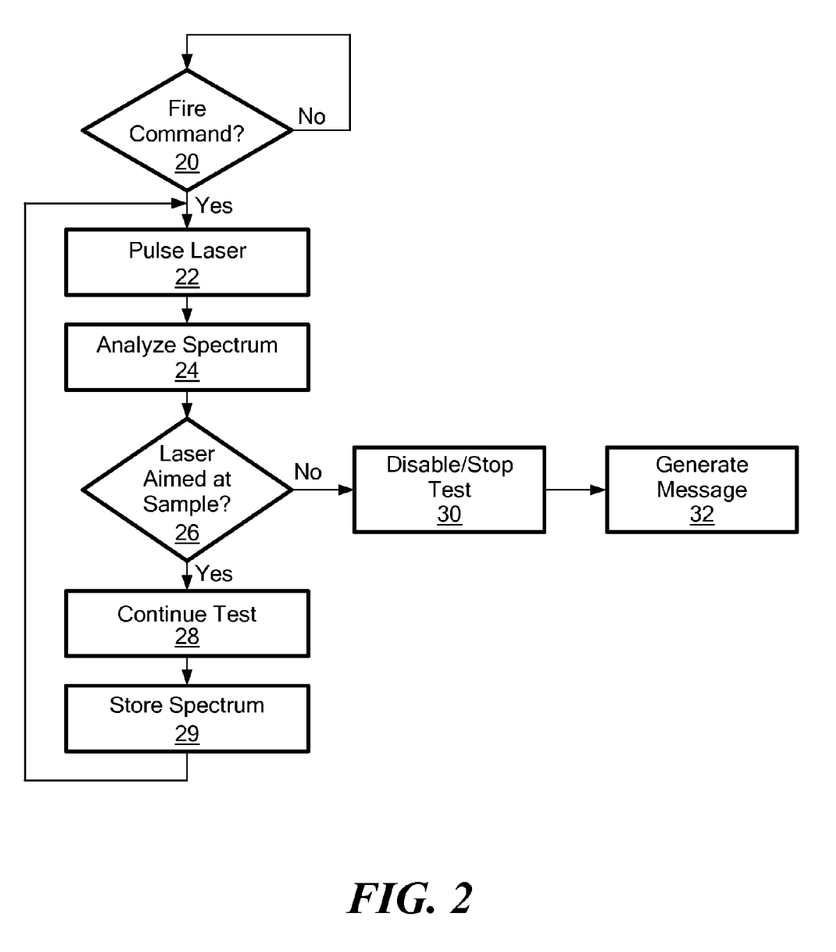
FIG. 2 is a flow chart depicting the primary steps associated with the preferred programming of the controller subsystem of FIG. 1 and also associated with one preferred method of the invention.

Here, controller subsystem 10 is configured (e.g., programmed) to energize laser 12 to pulse the laser, step 22, FIG. 2 when the operator (using input/output section 18) initiates a fire command, step 20 during a test. After the pulse, the resulting spectrum is analyzed, step 24, FIG. 2 and controller subsystem 10, FIG. 1, is configured to determine whether the laser is aimed at a sample to be analyzed or is instead aimed elsewhere (in air, for example).

Figure 3A:
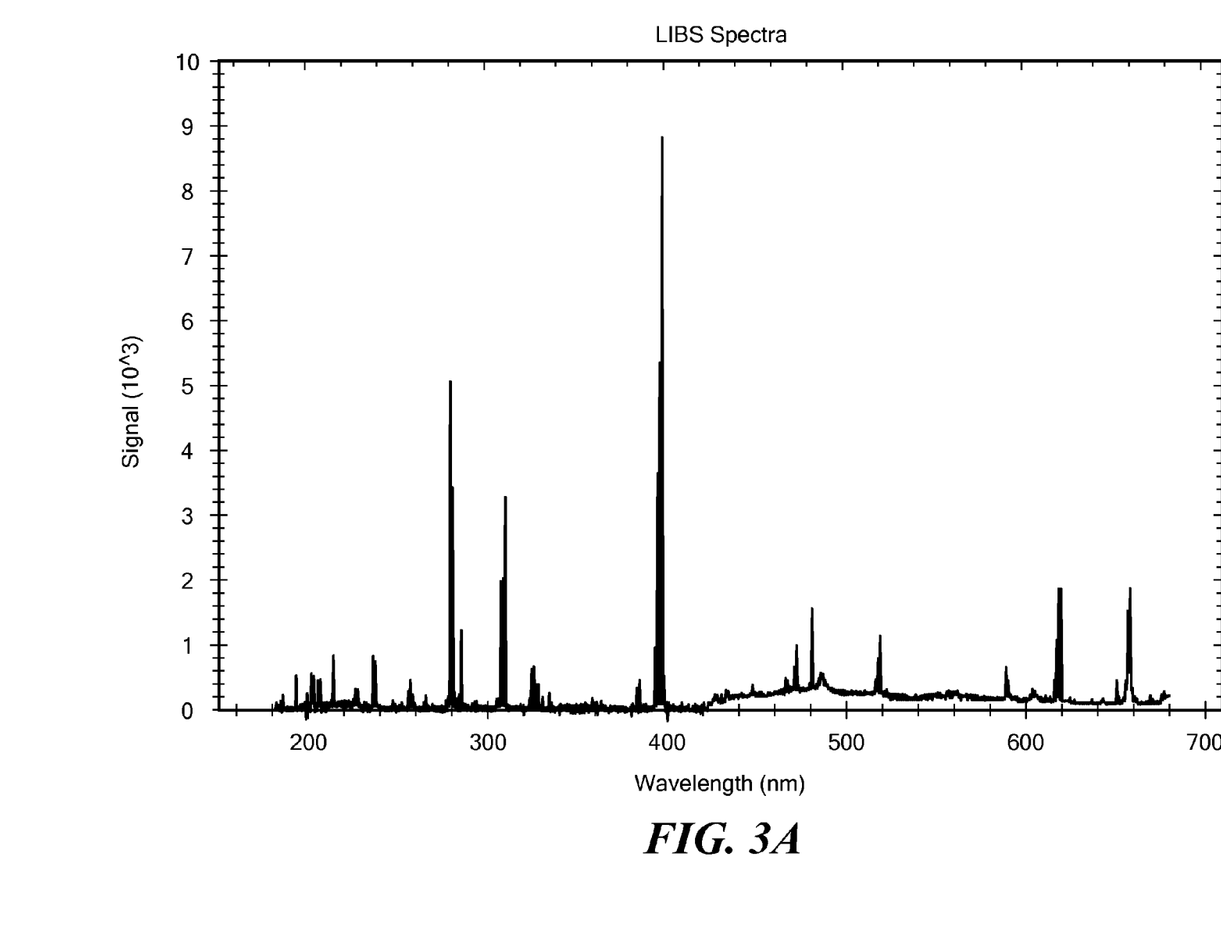
FIGS. 3A-3B are graphs showing a spectrum output by the spectrometer of FIG. 1 when the laser beam strikes a typical sample during a test.
Figure 3B:
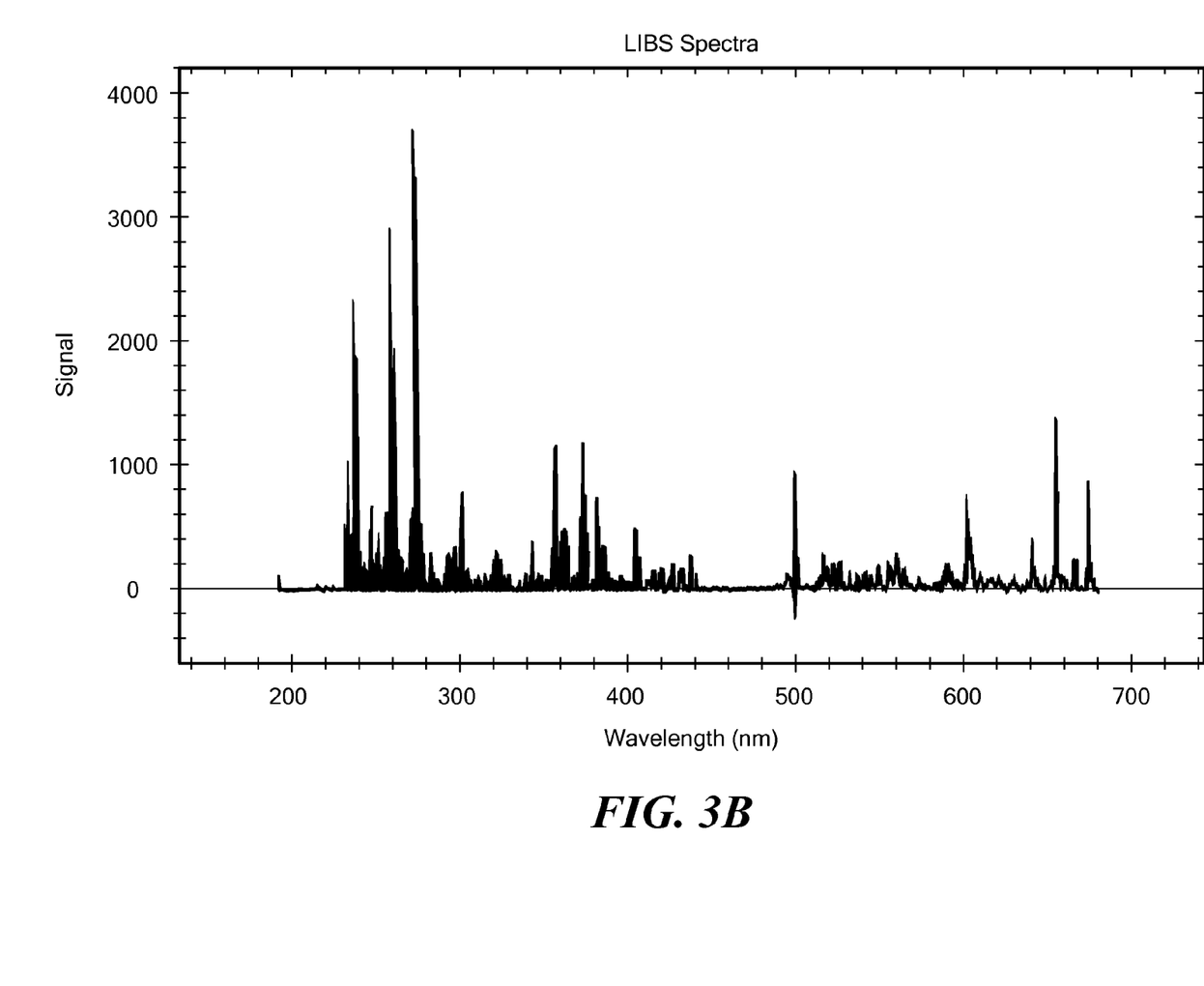

Shown in FIG. 3A is a typical spectrum where the nose section of the LIBS analyzer is placed directly on an aluminum sample and the laser is fired. FIG. 3B shows the spectrum produced for a steel sample. When such a spectrum is output by the spectrometer 14, FIG. 1, controller subsystem 10 automatically continues the test as shown at steps 26 and 28 by continuing to pulse the laser, for example at 10 Hz (or greater) while moving the laser over the sample between pulses (between pulses, the spectral dated is stored, step 29). Optional calibration cleaning, and/or autofocus routines may be carried out as well. During the test, the individual spectrums are preferably analyzed between laser pulses.

Figure 4:
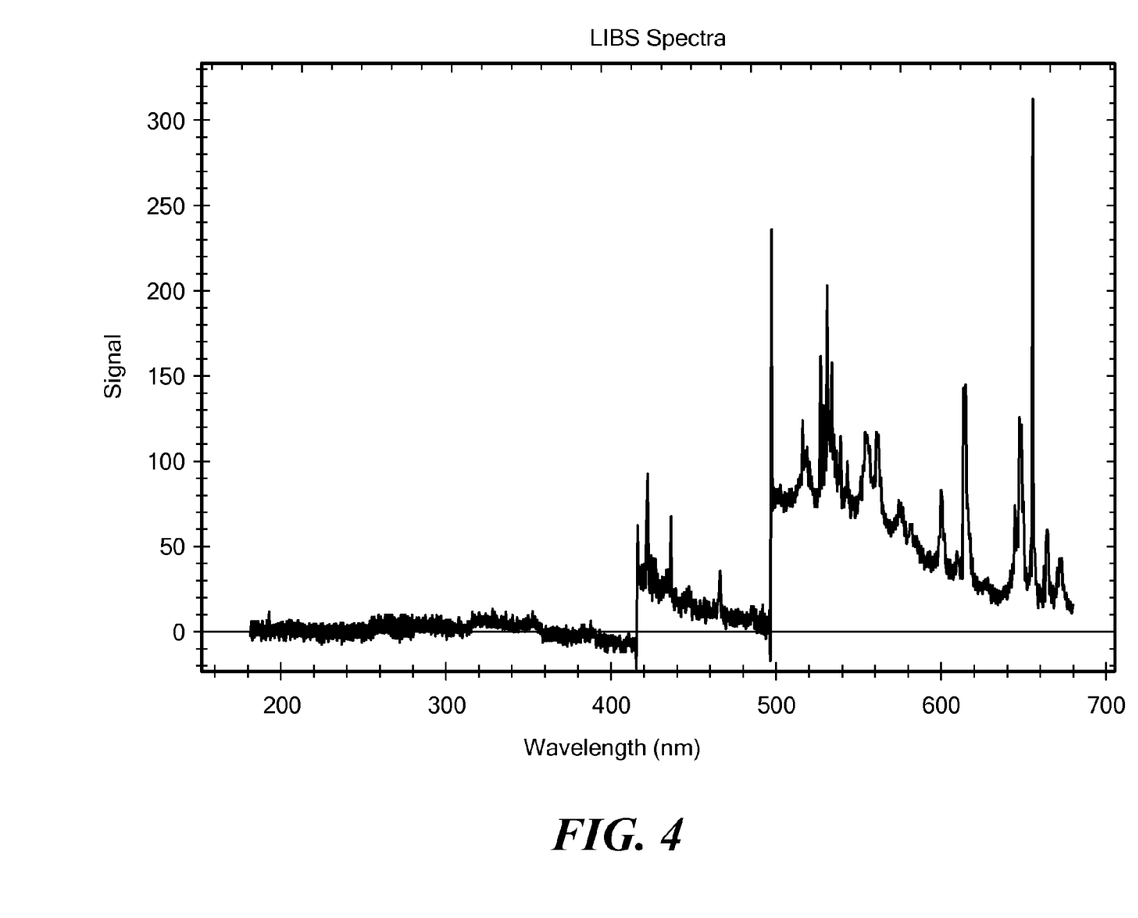
FIG. 4 is a depiction of an example of a spectrum output by the spectrometer of FIG. 1 when the laser beam output by the laser has failed to strike a sample proximate the LIBS analyzer.

If, however, an operator of the handheld LIBS device improperly triggers a fire command when the laser is aimed other than at a proximate sample (possibly even, at another person), then either no plasma will be produced and no spectrum is available for measurement or a plasma is produced in air—the spectrum of which is shown in FIG. 4. Note the highest peak is below 400 and there is no discernable signal at all below about 400 nm. When controller subsystem 10 detects the lack of a wavelength range (e.g., 200-400 nm) or a spectrum as shown in FIG. 4 or close approximations thereof, the laser is disabled and/or the test is stopped as shown at step 30, FIG. 2 automatically by the controller subsystem. The laser is not further pulsed as is the situation with a typical test of a sample. In addition, an error message may be generated by the controller subsystem as shown at step 32 for display on input/output section 18.

In some examples, controller subsystem 10, FIG. 1 searches database 16 for a spectrum matching that shown in FIG. 4, and if a match is found, further firing of the laser is prevented. The spectrums shown in FIG. 4 may be generated during controlled evaluations of the handheld LIBS unit by firing the laser such that the laser beam propagates through the air in a room, for example. Controller subsystem 10 may also reference one or more stored thresholds such that a peak detected below a threshold is indicative of the laser beam being fired through the air and not at a sample located proximate the nose section of the handheld LIBS analyzer.

In one example, the controller is programmed, for each pulse, to measure the maximum signal between a given wavelength range, e.g., between 200 and 400 nm. If the maximum signal there is below a predetermined level, e.g., 200, then the sample is not present (or has been moved relative to the hand held analyzer) and the normal laser pulse train sequence does not continue and the test is stopped.

Thus, if the operator has improperly aimed the laser at something other than a proximate sample to be tested, only one pulse of laser energy will be produced. The result is the same if the sample is removed during testing. As such, a higher power laser may be used (e.g., 3-8 mJ) for enhanced LIBS analysis and yet the handheld LIBS analyzer may still be classified as a Class I device. Thus, special training and/or equipment may not be required in order to operate such an analyzer.

According to the ANSI standard, a laser system with an emission duration of $10^{-7}$-$10^{-9}$ seconds at a wavelength of between 1,500-1,800 nm for an 8 mJ laser pulsed once meets the class I standard. Thus, by evaluating whether a sample is present for each pulse, laser 12, FIG. 1 may be an 8 mJ laser emitting at 1534 nm and, provided the emission duration (controlled by controller subsystem 10) is between $10^{-7}$-$10^{-9}$ seconds, the LIBS analyzer of FIG. 1 may be classified as a class I laser. When the sample is present and the pulse train continues during a test, then the accessible emission is blocked by the sample (which essentially serves as an interlock). Accordingly, the ANSI standard for class I lasers are met with the system shown. A safer system is also realized.

One preferred system is fault tolerant in that controller subsystem 10 includes two processors (e.g., a FPGA and an OMAP processor) processing the spectral data in real time. Assume a LIBS analyzer has a laser with a power P, a wavelength range $\lambda r$, and an emission duration t which meets the class I single pulse ANSI standard. Either processor will stop the laser pulse train at any time the maximum signal amplitude in an analyzed spectrum over a given wavelength range $\lambda_1$, is less than $A_1$. In one example, P was 8 mJ, $\lambda r$ was 1500-1800, t was $10^{-7}$-$10^{-9}$, $\lambda_1$ was 200-400 nm, and $A_1$ was 200. Note that as shown in FIGS. 3A and 3B typical samples have peaks far greater than 200 in the wavelength range 200-400 nm. If a signal greater than $A_1$ is present in the spectrum in wavelength range $\lambda_1$, the controller subsystem then automatically pulses the laser again. This process continues until the test is complete (typically 10-30 pulses as a typical test duration). If a sample is not present, is moved, if a spectrometer fails, or an optical fiber breaks, or the laser stops firing, the spectrum will not have a signal greater than $A_1$ in the wavelength range $\lambda_1$ and the test will be automatically stopped.

In another example, the laser has a wavelength of 1064 nm (at 10 mJ), and an emission duration which meets a class 3b safety standard. The spectrometer is responsive to radiation emitted by a plasma created by the laser beam and configured to produce a spectrum. The controller subsystem is configured to initiate a laser pulse sequence and analyze the resulting spectrum for each laser pulse. The controller halts the laser pulse sequence if a maximum signal amplitude in a predetermined wavelength range of the spectrum is less than a predetermined amplitude and continues pulsing the laser if the maximum signal amplitude in the predetermined wavelength range of the spectrum is greater than the predetermined amplitude. In this example, even though the laser class remains at a 3b rating, for misuse of the device, at most a single laser pulse can escape the device. Without the pulse spectral monitoring, an operator could fire a large number of laser pulses that miss the sample potentially striking an operator or bystander's eyes.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A LIBS analyzer comprising:
    a laser configured to produce a plasma on a sample;
    a spectrometer responsive to radiation emitted from the plasma and configured to produce a spectrum; and
    a controller subsystem configured to control energizing of the laser and including computer instructions which:
        initiate a laser pulse sequence in response to a fire command,
        analyze the resulting spectrum from each laser pulse to determine if the laser is aimed at a sample,
        if the analyzed spectrum reveals the laser is aimed at the sample, continue pulsing the laser to test the sample for a test duration; and
        if the analyzed spectrum reveals the laser is not aimed at the sample, halt the laser pulse sequence.

2. The LIBS analyzer of claim 1 in which testing the sample includes pulsing the laser at 10 Hz or greater and analyzing the spectrum between pulses.

3. The LIBS analyzer of claim 1 in which the controller subsystem is further configured to generate a message if the analyzed spectrum reveals the laser is not aimed at the sample.

4. The LIBS analyzer of claim 1 in which the laser has a power, a wavelength range, and an emission duration which meets the class I single pulse ANSI standard.

5. The LIBS analyzer of claim 4 in which the power is 8 mJ or less, the wavelength range is 1500-1800 nm, and the emission duration is $10^{-7}$-$10^{-9}$ seconds.

6. The LIBS analyzer of claim 4 in which analyzing the resulting spectrum for each laser pulse includes measuring the maximum signal in a predetermined wavelength range of the spectrum.

7. The LIBS analyzer of claim 6 in which the controller subsystem computer instructions automatically halt the laser pulse sequence if the maximum signal amplitude in a predetermined wavelength range of the spectrum is less than a predetermined amplitude.

8. The LIBS analyzer of claim 7 in which the predetermined amplitude is 200 and the predetermined wavelength range is 200-400 nm.

9. The LIBS analyzer of claim 6 in which the controller subsystem computer instructions automatically continues the test if the maximum signal amplitude in the predetermined wavelength range is greater than the predetermined amplitude.

10. A LIBS analysis method comprising:
    initiating a laser pulse sequence in response to a firing command;
    receiving radiation and providing a spectrum for each laser pulse;
    analyzing the spectrum to determine if the laser is aimed at a sample and producing a plasma on the sample;

continue pulsing the laser to test the sample if the analysis reveals the laser is aimed at the sample; and stopping the test if the analysis reveals the laser is not aimed at the sample.

11. The LIBS analyzer method of claim 10 in which testing the sample includes pulsing the laser at 10 Hz or greater and analyzing the spectrum between pulses.

12. The LIBS analyzer method of claim 10 further including generating a message if the analyzed spectrum reveals the laser is not aimed at the sample.

13. The LIBS analyzer method of claim 10 in which the laser has a power, a wavelength range, and an emission duration which meets the class I single pulse ANSI standard.

14. The LIBS analyzer method of claim 13 in which the power is 8 mJ or less, the wavelength range is 1500-1800 nm, and the emission duration is $10^{-7}$-$10^{-9}$ seconds.

15. The LIBS analyzer method of claim 13 in which analyzing includes measuring the maximum signal amplitude in a predetermined wavelength range of the spectrum.

16. The LIBS analyzer method of claim 15 including halting the laser pulse sequence if the maximum signal amplitude in a predetermined wavelength range of the spectrum is less than a predetermined amplitude.

17. The LIBS analyzer method of claim 16 in which the predetermined amplitude is 200 and the predetermined wavelength range is 200-400 nm.

18. The LIBS analyzer method of claim 15 including automatically continuing the test if the maximum signal amplitude in the spectrum in the predetermined wavelength range is greater than the predetermined amplitude.

19. A LIBS analyzer comprising:

a laser having a power, a wavelength range, and an emission duration which meets a class I single pulse laser standard;

a spectrometer responsive to radiation emitted by a plasma created by a laser beam from the laser on a sample and configured to produce a spectrum; and a controller subsystem configured to:

initiate a laser pulse sequence, analyze the resulting spectrum for each laser pulse, halt the laser pulse sequence if a maximum signal amplitude in a predetermined wavelength range of the spectrum is less than a predetermined amplitude, and continue pulsing the laser if the maximum signal amplitude in the predetermined wavelength range of the spectrum is greater than the predetermined amplitude.

* * * * *

UNITED STATES PATENT AND TRADEMARK OFFICE
CERTIFICATE OF CORRECTION

PATENT NO. : 9,664,565 B2  
APPLICATION NO. : 14/632419  
DATED : May 30, 2017  
INVENTOR(S) : Day et al.

It is certified that error appears in the above-identified patent and that said Letters Patent is hereby corrected as shown below:

On the Title Page

At (57), the last line of the Abstract:
"controller subsystem halts the laser puke sequence."
Should read:
--controller subsystem halts the laser pulse sequence.--

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*